United States Patent [19]

Wirth et al.

[11] Patent Number: 5,096,717
[45] Date of Patent: Mar. 17, 1992

[54] DOUBLE-COATED GRANULES OF DISODIUM PAMIDRONATE

[75] Inventors: Dagmar Wirth, Magden, Switzerland; Christian Bucher, Freiburg, Fed. Rep. of Germany

[73] Assignee: Ciba-Geigy Corporation, Ardsley, N.Y.

[21] Appl. No.: 577,420

[22] Filed: Sep. 4, 1990

[30] Foreign Application Priority Data

Sep. 7, 1989 [CH] Switzerland .................... 3245/89

[51] Int. Cl.$^5$ ........................... A61K 9/52; A61K 9/54
[52] U.S. Cl. ..................................... 424/490; 424/457; 424/458; 424/459; 424/461; 424/462; 424/468; 424/494; 424/497; 424/470; 424/489; 514/108
[58] Field of Search ................ 424/490, 493, 494, 495, 424/497, 457, 458

[56] References Cited

U.S. PATENT DOCUMENTS

| 4,263,273 | 4/1981 | Appelgren et al. | 424/490 |
| 4,711,880 | 12/1987 | Stahl et al. | 514/108 |
| 4,786,505 | 11/1988 | Lovgren et al. | 424/468 |
| 4,853,230 | 8/1989 | Lovgren et al. | 424/466 |
| 4,898,737 | 2/1990 | Panoz et al. | 424/490 |
| 4,983,401 | 1/1991 | Eichel et al. | 424/490 |

OTHER PUBLICATIONS

British Medical Journal 295, 1301–1305 (1987).
Br J. Cancer, 61, 123–125 (1990).
Gennaro A. (ed) Remington's Pharmaceutical Sciences 17 ed. Mack Publishing Company, pp. 1633–1643 (1985).

Primary Examiner—Thurman K. Page
Assistant Examiner—James M. Spear
Attorney, Agent, or Firm—Irving M. Fishman; Karen G. Kaiser

[57] ABSTRACT

The invention relates to an advantageous oral administration from the disodium pamidronate in capsules. These capsules are filled with double-coated granules. The inner coating is hydrophilic and elastic, and the outer coating is gastric juice-resistant and intestinal juice-soluble. The granules are distinguished by good gastric compatibility.

8 Claims, No Drawings

DOUBLE-COATED GRANULES OF DISODIUM PAMIDRONATE

The invention relates to a particularly advantageous oral administration form for disodium 3-amino-1-hydroxypropane-1,1-diphosphonate, to methods for the production of this administration form and to the use of this administration form in a therapeutic method for the elimination of disorders of calcium and/or phosphate metabolism.

3-Amino-1-hydroxypropane-1,1-diphosphonic acid and its salts, a process for the preparation of this acid and its industrial use as a calcium complex-forming detergent constituent has been described in German Examined Published Patent Application No. 2,130,794. The suitability of the said acid and its salts as a pharmaceutical active ingredient has been described in German Published Patent Application No. 2,405,254. The disodium salt—called disodium pamidronate in the following has already been investigated clinically as an antihypercalcaemic agent. Numerous publications verify the good activity of this compound against the particularly serious diseases osteoporosis, osteolysis as a result of metastases in the bone substance and Paget's disease.

An antihypercalcaemic compound must additionally be suitable for long-term therapy for several months or years. For long administration periods of this type, administration forms are necessary which make possible administration by the patient without outside help. Oral administration forms such as capsules or tablets should correspond to these requirements. However, "epigastric complaints" are mentioned in the British Medical J. Volume 295, 1301-1305 (1987), see page 1304, during clinical tests on patients after administration of capsules or tablets containing disodium pamidronate. A need therefore exists for oral administration forms having improved gastric compatibility.

For orally administered granules having a small diameter, in particular pellets having a diameter of less than about 1.5 mm, their accelerated gastric passage is characteristic. These can overcome the barrier function of the pylons, dependent on the quantity of the substances contained in the stomach. If the granules, in particular the pellets, are further coated with a gastric juice-resistant, intestinal juice-soluble coating, release of the active ingredient in the stomach, which is still possible despite relatively rapid further transport, can be essentially eliminated. The release then takes place in a controlled manner in the doudenum, where better absorption takes place. The active compound is absorbed more rapidly and to a larger extent in this part of the gastrointestinal tract in the stomach, so that the risk here of local excess concentrations and ulcer formation is reduced.

The production of disodium pamidronate granules which are to be coated with a gastric juice-resistant, intestinal juice-soluble coating agent is problematical if the customary spraying-on methods are used. The organic solvents used in such methods are disadvantageous for ecological reasons. When spraying aqueous dispersions onto the preformed granules, the water is made basic in contact with the alkaline-reacting active ingredient disodium pamidronate. As the coating agent must be soluble in the basic medium because of the solubility required in the intestinal juice, granules containing this basically reacting active ingredient are unsuitable for coating with such a coating agent in the presence of water.

The invention is based on the object of coating granules of disodium pamidronate, in particular in the form of pellets, with a gastric juice-resistant, intestinal juice-soluble coating agent in such a way that this forms a solid and uniform coating on spraying-on using an aqueous dispersion of the coating agent despite incompatibility with the basically reacting active ingredient.

This object is achieved by the present invention by first coating the granules to be coated, preferably pellets, with a hydrophilic, elastic inner coating and then coating the granules protected in this way with a gastric juice-resistant, intestinal juice-soluble outer coating.

In a particularly preferred embodiment, the double-coated granules are formed as spherical pellets having a particle size of less than 1.5 mm.

The present invention relates to double-coated granules for the oral administrations of disodium pamidronate with controlled release, wherein the granules are coated with a hydrophilic, elastic inner coating and with a gastric juice-resistant, intestinal juice-soluble outer coating.

The double-coated granules, in particular pellets, are distinguished by good gastric compatibility. They are therefore particularly suitable for oral administration in capsules and for taking over relatively long periods of time.

The terms used further above and in the following are defined as follows in the context of the description of the invention:

In the double-coated granules according to the present invention, the active ingredient disodium pamidronate is preferably present in the form of its crystalline hydrate, in particular the pentahydrate, which is described in European Patent Application Publication No. 177,443.

Granules are solid pharmaceutical preparations which contain the active ingredient disodium pamidronate and those adjuncts which are customary in pharmaceutical technology for tableting methods. The granules according to the present invention can themselves be used as oral administration forms, but can also be further processed to give tablets.

Granules having a regular shape, for example rod-shaped or cylindrical, in particular ball-shaped, for example spherical or ellipsoidal, which are obtained by extrusion of the moist granulation material through nozzles, rounding-off and drying are preferred.

Ball-shaped, spherical pellets having a diameter between about 0.3 and 1.5 mm, in particular between about 0.5 and 1.25 mm, are preferred.

Adjuncts suitable for the production of the granules or pellets are, for example, pulverulent fillers, for example microcrystalline cellulose, for example of the Avicel ® type (FMC Corp.), for example of the types A VICEL PH 101, 102, 105, RC 581 or RC 591, Emcocel ® (Mendell Corp.) or Elcema ® (Degussa), carbohydrates such as sugar, sugar alcohols, starch or starch derivatives, for example lactose, dextrose, sucrose, glucose, sorbitol, mannitol, xylitol, potato, corn, rice or wheat starch or amylopectin, tricalcium phosphate, calcium hydrogen phosphate or magnesium trisilicate, binders such as cellulose ethers, for example methylcellulose, carboxymethylcellulose or hydroxypropylmethylcellulose, polyethylene glycols or ethylene oxide homopolymers, in particular having a degree of polymerization of about $2.0 \times 10^3 - 1.0 \times 10^5$ and an approximate molecular weight of about $1.0 \times 10^5$ to $5.0 \times 10^6$, for example adjuncts known under the name Polyox ® (Union Carbide), polyvinylpyrrolidone or povidone, in particular having an average molecular weight of about 10,000–360,000, polyvinyl alcohol having a degree of hydrolysis of about 95–98% and a degree of polymerization of about 500–2,500, and also agar or gelatin, surface-active substances, for example anionic surfactants of the alkyl sulfate type, for example sodium, potassium or magnesium n-dodecyl sulfate, n-tetradecyl sulfate, n-hexadecyl sulfate or n-octadecyl sulfate, an alkyl ether sulfate, for example sodium, potassium or magnesium n-dodecyloxyethyl sulfate, n-tetradecyloxyethyl sulfate, n-hexadecyloxyethyl sulfate or n-octadecyloxyethyl sulfate or an alkanesulfonate, for example sodium, potassium or magnesium n-dodecanesulfonate, n-tetradecanesulfonate, n-hexadecanesulfate or n-octadecanesulfonate, non-ionic surfactants of the fatty acid polyhydroxy alcohol ester type such as sorbitan monolaurate, oleate, stearate or palmitate, sorbitan tristearate or trioleate, polyoxyethylene adducts of fatty acid polyhydroxy alcohol esters such as polyoxyethylene sorbitan monolaurate, oleate, stearate, palmitate, tristearate or trioleate, polyethylene glycol fatty acid esters such as polyoxyethyl stearate, polyethylene glycol 400 stearate, polyethylene glycol 2000 stearate, in particular ethylene oxide/propylene oxide block polymers of the Pluronics ® type (BWC) or Synperonic ® (ICI).

The term "oral administration of disodium pamidronate" defines the utility of the double-coated granules, preferably pellets, as oral administration forms, in that the double-coated granules are filled, for example, into capsules or sachets.

Capsules are preferably dry-filled capsules made of gelatin (hard gelatin) which, if desired, are prepared with the addition of glycerol or sorbitol, dissolve as a result of the action of gastric juice without delay and at the same time initially release the double-coated granules or pellets. These are transported further into the duodenum through the pylorus. Depending on the dosage, dry-filled capsules of sizes 0–4, preferably 0–2, are suitable. The capsules can be transparent, colourless or coloured and also, if desired, labelled in order to impart individual appearance or immediate recognizability to them. The goods of the firms Eli Lilly, Elanco, Capsugel or Scherer are suitable.

Sachets are containers, for example bags made of polyethylene, lined paper or aluminium, which contain the double-coated granules. After opening, the granules can be taken immediately.

The term "controlled release" defines an influencing of the release ("targeting") of the active ingredient sodium pamidronate that essentially takes place with the main quantity in the duodenum and, if appropriate, with a residual amount in the jejunum after the gastric passage of the administration form.

The hydrophilic, elastic inner coating of the double-coated granules consists of a film-like material which is permeable to water or gastric juice and can be swollen and is at least partially soluble in these fluids. The inner coating prevents the alkaline reaction of the active ingredient disodium pamidronate with the aqueous dispersion of the gastric juice-resistant, small intestinal juice-soluble coating agent.

Film-like materials having water permeability are, for example, hydrophilic mixtures of polyvinylpyrrolidone or a copolymer of polyvinylpyrrolidone and polyvinyl acetate with hydroxypropylmethylcellulose, mixtures of shellac with hydroxypropylmethylcellulose, polyvinyl acetate or its copolymers with polyvinylpyrrolidone, or mixtures of water-soluble cellulose derivatives, such as hydroxypropylmethylcellulose, and water-insoluble ethylcellulose.

These actual coating agents can be used, if desired, in a mixture with other adjuncts, such as talc or silica, for example synthetic amorphous silicic acid of the Syloid ® type (Grace), for example SYLOID 244 FP, or wetting agents, for example the polyethylene glycols or sorbates mentioned further above.

Elastic, film-like materials are, in particular, hydrophilic, partially etherified cellulose derivatives.

Hydrophilic, partially etherified cellulose derivatives are, for example, lower alkyl ethers of cellulose with an average degree of molar substitution (MS) of greater than one and smaller than three and an average degree of polymerization of about 100–5,000.

The degree of substitution is a measure of the substitution of the hydroxyl groups by lower alkoxy groups per glucose unit. The average degree of molar substitution (MS) is a standardized value and indicates the number of lower alkoxy groups per glucose unit in the polymer.

The average degree of polymerization (DP) is also a standardized value and indicates the average number of glucose units in the cellulose polymer.

Lower alkyl ethers of cellulose are, for example, cellulose derivatives which are substituted on the hydroxymethyl group (primary hydroxyl group) of the glucose unit forming the cellulose chains and, if appropriate, on the second and third secondary hydroxyl group by $C_1$–$C_4$alkyl groups, in particular methyl or ethyl, or by substituted $C_1$–$C_4$alkyl groups, for example 2-hydroxyethyl, 3-hydroxy-n-propyl, carboxymethyl or 2-carboxyethyl.

Suitable lower alkyl ethers of cellulose are preferably cellulose derivatives which are substituted on the hydroxymethyl group (primary hydroxyl group) of the glucose units by the said $C_1$–$C_4$alkyl groups or by substituted $C_1$–$C_4$alkyl groups and on the second and, if appropriate, third secondary hydroxyl group by methyl or ethyl groups.

Suitable lower alkyl ethers of cellulose are, in particular, methylcellulose, ethylcellulose, methylhydroxyethylcellulose, methylhydroxypropylcellulose, ethylhydroxyethylcellulose, hydroxyethylcellulose, hydroxypropylcellulose, carboxymethylcellulose (in salt form, for example as the sodium salt) or methylcarboxymethylcellulose (also in salt form, for example as the sodium salt).

Preferred lower alkyl ethers of cellulose are methylcellulose (DP: about 200–1000, MS: about 1.4–2.0), ethylcellulose (DP: about 150–1000, MS: about 1.2–1.8), for example of the Aquacoat ® type (FMC Corp.), hydroxyethylcellulose (DP: about 120–1200, MS: about 1.2–2.5), hydroxypropylcellulose (DP: about 200–3000, MS: about 1.0–3.0) and methylhydroxypropylcellulose (DP: about 200–1000, MS: about 1.4–2.0), for example of the Pharmacoat ® type (Shin Etsu Corp.).

The gastric juice-resistant, intestinal juice-soluble outer coating consists of a film-like material which is permeable to water under the acidic pH conditions of the gastric juice and is soluble under the neutral to weakly basic conditions of the intestinal juice, in particular in the duodenum.

This film-like material can be applied from an aqueous dispersion to the granules or pellets which have previously been provided with the hydrophilic, elastic inner coating.

Film-like materials having water solubility under neutral to alkaline conditions are, for example, cellulose acetate esters, for example cellulose acetate phthalate (CAP), cellulose acetate trimellitate (CAT) or methacrylic acid-methacrylate 1:1 or 1:2 copolymer, for example EUDRAGIT L and S, for example EUDRAGIT L 12.5 or S 12.5.

Preferably, the film-like material is sprayed on as an aqueous dispersion of redispersible cellulose acetate phthalate - CAP - (Aquateric ®: FMC), polyvinyl acetate phthalate-PVAP - (Coateric ®: Colorcon), hydroxypropylmethylcellulose phthalate - HPMCP (Aquacoat ®: Shin-Etsu) and, in particular, acrylic acid-methacrylic acid copolymer partially esterified by $C_1$–$C_4$ alkyl groups.

In particular, an acrylic acid-methacrylic acid 1:1 copolymer partially esterified by methyl and/or ethyl groups of the type EUDRAGIT L 30 D or water-dispersed EUDRAGIT L 100-55 is used.

The film-like material of the outer gastric juice-resistant, intestinal juice-soluble outer coating preferably contains additional adjuncts such as plasticizers, for example triethyl citrate, for example Citroflex ® (Pfizer), triacetin, various phthalates, for example diethyl phthalate or dibutyl phthalate, mixed mono- or diglycerides of the Myvacet ® type (Eastman), for example MYVACET 9-40, the polyethylene glycols mentioned further above, for example having a molecular weight of about 6000–8000 and also ethylene oxide-propylene oxide block copolymers of the type Pluronic ® (BASF) or Synperonic ® (ICI), pulverulent mould-release agents, for example titanium dioxide, talc, magnesium trisilicate, starch or synthetic amorphous silicic acid of the type SYLOID, for example SYLOID 244 FP.

The aqueous dispersion may additionally contain surface-active substances such as ANTIFOAM AF in order to prevent the formation of foam.

The invention preferably relates to pellets of the ground, crystalline pentahydrate which are coated with a hydrophilic, elastic inner coating of hydroxypropylmethylcellulose and a gastric juice-resistant, intestinal juice-soluble outer coating of an acrylic acid-methacrylic acid 1:1 copolymer which is partially esterified by $C_1$–$C_4$ alkyl groups and contain up to 90% by weight of active ingredient.

The invention also relates to the use of disodium pamidronate, in particular the crystalline pentahydrate, for the production of a solid pharmaceutical administration form, preferably capsules or sachets, containing double-coated granules having controlled release and to these administration forms themselves.

The production of granules containing disodium pamidronate is carried out in a manner known per se using methods for the production of build-up or break-down granules.

Build-up granules are formed by continuous methods, for example by simultaneously spraying the granulation material with a granulation solution and drying, for example in the granulating drum, in granulating vessels, or granulating discs, in a fluidized bed, by spray drying or spray solidification or discontinuously, for example in the fluidized bed, in a batch mixer or in the spray drying drum.

Preferred methods for the production of break-down granules are those which take place batchwise, in that the granulation material initially forms a moist aggregate with the granulation solution which is subsequently disintegrated to give granules, in particular pellets, having the desired grain size, known extrusion and sphere-forming methods being used. Suitable extruders and rounders are, for example, devices from the firms Wyss & Probst, Werner & Pfleiderer, HKD, Loser, Fuji, Nica and Caleva, inter alia.

The granulation material consists of the comminuted, preferably ground active ingredient disodium pamidronate, preferably having an average particle size of less than 400 μm (more than 90%) and the other adjuncts mentioned further above, for example pulverulent fillers such as microcrystalline cellulose of the A VICEL type. A VICEL PH 105 is particularly suitable. Depending on the method used, the granulation material can be premixed or obtained by admixing ADP $Na_2$ to one or more adjuncts or by admixing the adjuncts to disodium pamidronate.

Preferably, pellets having a spheroidal shape and a particle size of about 0.5 to 1.25 mm are prepared.

The coating of the granules or the pellets with the hydrophilic, elastic inner coating is carried out in a manner known per se using customary coating methods.

For example, the coating agent is dissolved or suspended in water in the desired quantity ratio. If appropriate, adjuncts such as polyethylene glycol re added. This solution or dispersion is sprayed onto the granules or pellets with other adjuncts, for example talc or silica, for example SYLOID 244 FP, for example using known methods, such as spray coating in the fluidized bed, for example in the systems by Aeromatic, Glatt, Wurster or Hüttlin (ball coater) and also is the vessel by the methods known under the names Accela Cota or dipping tube method.

Preferably, an aqueous dispersion containing hydroxypropylmethylcellulose (cellulose HPM) is sprayed on.

The coating of the granules or pellets, previously coated with the hydrophilic, elastic inner coating, with the gastric juice-resistant, intestinal juice-soluble outer coating can be carried out in a manner known per se by those methods which have previously been used for the coating of the granules with the inner coating.

Preferably, an acrylic acid-methacrylic acid 1:1 copolymer of the EUDRAGIT L 30 D type is sprayed on as an aqueous dispersion in the fluidized bed with the addition of plasticizers such as triethyl citrate, antifoam agents and amorphous silica, for example SYLOID 244 FP.

The double-coated granules or pellets are then filled into capsules, preferably hard gelatin capsules of size 0, if appropriate with the addition of glidants such as talc or amorphous silica. The filling operation can be carried out using one of the commercial capsule filling machines, for example machines of the Höfliger and Karg, Macofar or MG2 type. The capsules may in turn be filled into blister packs or containers made of glass or polyethylene.

The solid pharmaceutical dosage forms of the present invention are distinguished by particularly good gastrointestinal compatibility of the active ingredient disodium pamidronate. The administration forms are suitable for the treatment of diseases which can be associated with disorders of the calcium metabolism, for example inflammatory processes in joints, degenerative processes in the joint cartilage, osteoporosis, periodontitis, hyperparathyroidism, and of calcium deposits in blood vessels or on prosthetic implants. Disorders in which an anomalous deposit of sparingly soluble calcium salts can be detected, such as those from the arthritis group, for example Bechterew's disease, neuritis, bursitis, periodontitis and tendinitis, fibrodysplasia, osteoarthritis or arteriosclerosis, and those in which an anomalous dissolution of hard body tissue is prominent, such as hereditary hypophosphatasia, degenerative processes in the joint cartilage, osteoporoses of various geneses, Paget's disease and osteodystrophia fibrosa, as well as osteolytic processes caused by tumours and hypercalcaemia, are favourably influenced.

Consequently, the present invention also relates to the use of the solid pharmaceutical administration forms in a therapeutic or prophylactic method for the human or animal body.

The following examples illustrate the invention Disodium pamidronate is abbreviated: APD $Na_2$.

| Example 1: | |
|---|---|
| Core pellet: | |
| APD $Na_2$ pentahydrate (ground) ($\hat{=}$150 mg of anhydrous active ingredient) | 197.3 mg |
| Microcrystalline cellulose (Avicel ® PH 105) | 52.7 mg |
| | 250.0 mg |
| Inner coating: | |
| Cellulose HP-M 603 | 10.0 mg |
| Polyethylene glycol | 2.0 mg |
| Talc | 8.0 mg |
| | 270.0 mg |
| Gastric juice-resistant outer coating: | |
| Eudragit ® L 30 D (solid) | 90.0 mg |
| Triethyl citrate | 21.0 mg |
| Antifoam ® AF | 2.0 mg |
| Water | |
| Talc | 7.0 mg |
| | 390.0 mg |

A mixture of APD $Na_2$ with Avicel ® PH 105 is moistened with water and kneaded, extruded and formed into spheres. The dried pellets are then successively coated in the fluidized bed with an inner coating, consisting of cellulose HP-M 603, polyethylene glycol (PEG) 8000 and talc, and the aqueous gastric juice-resistant coat, consisting of Eudragit ® L 30 D, triethyl citrate and Antifoam ® AF. The coated pellets are powdered with talc and filled into capsules (capsule size 0) by means of a commercial capsule filling machine, for example Höfliger and Karg.

EXAMPLE 2

| Core pellets: | |
|---|---|
| APD $Na_2$ pentahydrate (ground) | 197.3 mg |
| Microcrystalline cellulose (Avicel ® PH 105) | 52.7 mg |
| | 250.0 mg |
| Inner coating: | |
| Cellulose HP-M 603 | 10.0 mg |
| PEG 8000 | 2.0 mg |
| Talc | 8.0 mg |
| | 270.0 mg |
| Gastric juice-resistant outer coating: | |
| Eudragit L 30 D (solid) | 90.0 mg |
| Triethyl citrate | 21.0 mg |
| Antifoam ® AF | 1.0 mg |
| Syloid ® 244 FP | 9.0 mg |
| Water | |

| -continued | |
|---|---|
| Talc | 4.0 mg |
| | 395.0 mg |

A procedure analogous to Example 1 is used and SYLOID amorphous silica is added to the outer coating.

EXAMPLE 3

| Core pellet: | |
|---|---|
| APD $Na_2$ pentahydrate/WS | 197.3 mg |
| Microcrystalline cellulose (Avicel ® PH 105) | 52.7 mg |
| | 250.0 mg |
| Inner coating: | |
| Cellulose HP-M 603 | 10.0 mg |
| PEG 8000 | 2.0 mg |
| Syloid ® 244 FP | 8.0 mg |
| | 270.0 mg |
| Gastric juice-resistant outer coating: | |
| Eudragit ® L 30 D (solid) | 90.0 mg |
| Triethyl citrate | 21.0 mg |
| Antifoam ® AF | 1.0 mg |
| Syloid ® 244 FP | 9.0 mg |
| Water | |
| Talc | 4.0 mg |
| | 395.0 mg |

A procedure analogous to Example 1 is used, talc is replaced by SYLOID for the inner coating and SYLOID is additionally added to the outer coating.

What is claimed is:

1. Granules for the oral administration of disodium 3-amino-1-hydroxypropane-1,1-diphosphonate (disodium pamidronate) having a double coating and controlled release, wherein the granules are formed as spherical pellets having a diameter of about 0.3 to about 1.5 mm and coated with a hydrophilic, elastic inner coating and a gastric juice-resistant, intestinal juice-soluble outer coating.

2. A method for the production of granules according to claim 1, wherein disodium pamidronate is granulated the granules are provided with a hydrophilic, elastic inner coating and then coated with a gastric juice-resistant, intestinal juice-soluble outer coating.

3. A solid pharmaceutical administration form for the oral administration of the crystalline pentahydrate of disodium pamidronate in the form of capsules or sachets containing double-coated granules having controlled release, wherein the granules are formed as spherical pellets and coated with a hydrophilic, elastic inner coating and a gastric juice-resistant, intestinal juice-soluble outer coating.

4. Granules according to claim 1, wherein the diameter of said spherical pellets is about 0.5 to 1.25 mm.

5. Granules according to claim 1, wherein said hydrophilic, elastic inner coating comprises a cellulose ether.

6. Granules according to claim 5, wherein these are coated with a hydrophilic, elastic inner coating of hydroxypropylmethylcellulose.

7. Granules according to claim 1, wherein said gastric juice-resistant, intestinal juice-soluble outer coating comprises an acrylic acid-methacrylic acid copolymer which is partially esterified by $C_1$–$C_4$alkyl groups.

8. Granules according to claim 7, wherein these are coated with a gastric juice-resistant, intestinal juice-soluble outer coating of an acrylic acid-methacrylic acid copolymer which is partially esterified by methyl and/or ethyl groups.

* * * * *